United States Patent
Neuberger et al.

(10) Patent No.: US 6,503,268 B1
(45) Date of Patent: *Jan. 7, 2003

(54) THERAPEUTIC LASER SYSTEM OPERATING BETWEEN 1000NM AND 1300NM AND ITS USE

(75) Inventors: Wolfgang Neuberger, F.T. Labuan (MY); Hans-Joachim Schwarzmaier, Düsseldorf (DE)

(73) Assignee: CeramOptec Industries, Inc., East Longmeadow, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/541,953

(22) Filed: Apr. 3, 2000

(51) Int. Cl.[7] ............................................. A61B 18/18
(52) U.S. Cl. ................................. 607/89; 606/2; 606/3
(58) Field of Search ............... 606/2, 3–16; 607/88–89, 607/92

(56) References Cited

U.S. PATENT DOCUMENTS

| | | | | |
|---|---|---|---|---|
| 5,187,672 A | * | 2/1993 | Chance et al. | 364/550 |
| 5,353,799 A | * | 10/1994 | Chance | 128/664 |
| 5,636,238 A | * | 6/1997 | Mohebati et al. | 372/54 |
| 5,664,574 A | * | 9/1997 | Chance | 128/664 |
| 5,861,020 A | | 1/1999 | Schwarzmaier | |
| 5,989,246 A | | 11/1999 | Raimund et al. | |
| 6,059,820 A | * | 5/2000 | Baronov | 607/89 |
| 6,149,671 A | * | 11/2000 | Nordquist et al. | 607/89 |
| 6,214,033 B1 | * | 4/2001 | Ii et al. | 604/20 |

* cited by examiner

Primary Examiner—Michael Peffley
Assistant Examiner—Peter J Vrettakos
(74) Attorney, Agent, or Firm—Bolesh J. Skutnik; BJ Associates

(57) ABSTRACT

Laser systems medical or cosmetic applications, comprising diode lasers or diode lasers with other solid state lasers which can deliver up to 30 cw or more, and which generally operate at more than wavelength within the range of 1000 to 1300 nm are presented. Individual emitter or emitter groups within the diode laser system can be powered independently. These laser systems provide maximum penetration depths for procedures such as Laser-induced Interstitial Tumor Therapy, alone or in conjunction with other therapies such as PhotoDynamic Therapy, chemotherapy, or radiation therapy. Where beneficial for the procedure, the operating wavelength of the system can be changed without interruption. In some variants, active tissue cooling at the distal end of the delivery fibers is incorporated as well as individual feedback loops to control and stabilize the temperature induced in the tissue. To enhance thermal or photo effects and thereby increase efficiencies, absorbers can be administered and the laser system tuned to the specific absorption band of the absorber.

9 Claims, 3 Drawing Sheets

THERAPEUTIC LASER SYSTEM OPERATING BETWEEN 1000NM AND 1300NM AND ITS USE

BACKGROUND OF THE INVENTION

1. Field of Invention

The field of the invention is diode laser systems used for medical or cosmetic treatments in the thermal regime alone or in conjunction with other therapies such photodynamic therapy, chemotherapy or radiation therapy.

2. Information Disclosure Statement

A lot of different tumor types, located in various parts of the body have been successfully treated with lasers in the recent years. In this way, lasers have also been used for the thermal destruction of tumors. This therapy is called laser-induced interstitial tumor therapy (LITT). The target tissue (a tumor) is irradiated with laser light using a specially designed light guide ending in an adequate applicator (e.g. cooled optical diffuser).

The light generated by a laser is absorbed selectively by tissue, because of its monochromatic and coherent nature. This absorption is dependent on the physical properties of the tissue, which include absorption and scattering. These properties depend on the wavelength of the incident laser light. Absorption in tissue is mainly characterized by water absorption, because in the infrared region there is a very large and sharp vibrational absorption band for water.

The laser light absorbed by the tissue is leading to heating of the target volume. The resulting thermal damage leads to the destruction of the tumor. The primary effect here is the direct coagulation of the irradiated tissue, while temperature dependent, also other mechanisms are described (e.g. hyperthermia).

Up to now the therapy was conducted with Nd-YAG lasers. This laser was used because there is a local absorption minimum in water at 1050 nm. At this wavelength the laser light is absorbed mainly by blood and not by water. This leads to a penetration depth, which is sufficient for a successful therapy. This means that the laser light penetrates a certain depth into the tissue before it is absorbed. Although the Nd-YAG laser is commonly used for interstitial tumor therapy, the use of this single wavelength is based primarily on the fact, that no other lasers in this wavelength range were available. Additionally this type of laser requires a lot of maintenance and costly techniques.

Due to new developments this limited approach can be overcome. Diode laser light sources will now be available in the wavelength range of 1000 nm up to 1300 nm. These laser are almost maintenance free and easy to use.

Additionally studies based on recent measurements surprisingly show that the maximum penetration depth is not located at a wavelength of 1064 nm, but in the wavelength range of 1100 nm to 1150 nm. These measurements take into account, that the penetration depth is not only dependent on the absorption of water. For this the absorption and scattering of the other ingredients of tissue also have to be taken into account. A measurement of the absorption and scattering properties of tissue (for example in brain tumors as described below) show that the penetration depth in the entire wavelength range of 1000 nm up to 1300 nm is similar to that at 1064 nm with a maximum from 1100 nm to 1150 nm. Consequently these wavelengths are also very suitable to be used for the LITT. This wavelength region has not been used in the prior art, because no adequate laser light sources (with powers of 30 W cw) were available until now.

Large penetration depths are especially important for cooled LITT (U.S. Pat. Nos. 5,989,246 and 5,861,020). These systems are used to cool the area surrounding the applicator. Therefore, a larger power can be applied without inducing carbonization or vaporization in this area. This results in even bigger lesion sizes. Having maximum penetration depths would thus help treat large areas, quicker and with less treatments.

During the coagulation process the denaturation of the proteins leads to a change of the physical properties (optical, thermal, perfusion, . . . ). Usually the denaturation leads to higher scattering and lower absorption in tissue. This means that the penetration depth will change. A large penetration depth could then be achieved by increasing the wavelength of the used laser. Therefore, it may be required to change the laser wavelength, as a consequence of the coagulation process.

The limitation to only one wavelength, in the current art, presents a number of drawbacks. The Nd-YAG equipment used by physicians in the clinics today are quite bulky and require a lot of maintenance. Moreover the laser and the wavelength used right now does not allow the maximal penetration depth, which could be achieved with laser diodes. Additionally by adjusting the wavelength one would be able to adapt to the different optical properties of different tissue types, and thereby achieve the best success in therapy. Having multiple wavelengths available in a compact diode laser package would allow the possibility of a combination with other existing therapies which could lead to new therapeutic techniques. Thus far however diode lasers operating above 1000 nm have not been available.

SUMMARY AND OBJECTIVES OF THE INVENTION

It is therefore an object of this invention to provide a novel family of laser systems comprising diode lasers or diode lasers with other solid state lasers for performing medical or cosmetic procedures such as Laser-induced Interstitial Tumor Therapy (LITT) treatments on large tumors or ones needing high penetration depths, and which can operate at more than one wavelength in the wavelength range of 1000 nm to 1300 nm and more optimally between 1100 to 1300 nm.

It is another object of this invention to provide diode laser systems with at least two emitters or emitter groups, each of which is coupled to an optical fiber or waveguide.

A further object of this invention is to provide a diode laser system where each single emitter or emitter group can be individually controlled in power.

A still further object of this invention is to incorporate within the system means to provide active tissue cooling at the distal end of the fibers or waveguides and/or to provide individual feedback loops for each single emitter or emitter group to control and stabilize the temperature induced in the tissue.

Yet another object of this invention is to provide a method for a surgical or cosmetic laser procedure, such as laser-induced interstitial tumor therapy, using a diode laser system operating at wavelengths between 1000 nm and 1300 nm and where delivery to interior sites employs interstitial fibers or waveguides.

Still another object of this invention is to provide a method for a surgical or cosmetic laser procedure which can be combined with chemotherapy or radiation therapy to enhance the therapeutic effects of both therapies.

Another object of this invention is to provide a laser system which can be tuned to the absorption band of an absorber, which has been introduced to the treatment site prior to irradiation.

Briefly stated the present invention provides laser systems for medical or cosmetic applications, comprising diode lasers or diode lasers with other solid state lasers which can deliver up to 30 cw or more, and which generally operate at more than wavelength within the range of 1000 to 1300 nm. Individual emitter or emitter groups within the diode laser system can be powered independently. These laser systems provide maximum penetration depths for procedures such as Laser-induced Interstitial Tumor Therapy, alone or in conjunction with other therapies such as PhotoDynamic Therapy, chemotherapy, or radiation therapy. Where beneficial for the procedure, the operating wavelength of the system can be changed without interruption. In some variants, active tissue cooling at the distal end of the delivery fibers is incorporated as well as individual feedback loops to control and stabilize the temperature induced in the tissue. To enhance thermal or photo effects and thereby increase efficiencies, absorbers can be administered and the laser system tuned to the specific absorption band of the absorber.

The above, and other objects, features and advantages of the present invention will become apparent from the following detailed description read in conjunction with the accompanying drawings.

DETAILED DESCRIPTION OF THE PREFERRED EMBODIMENTS

Figure 1:
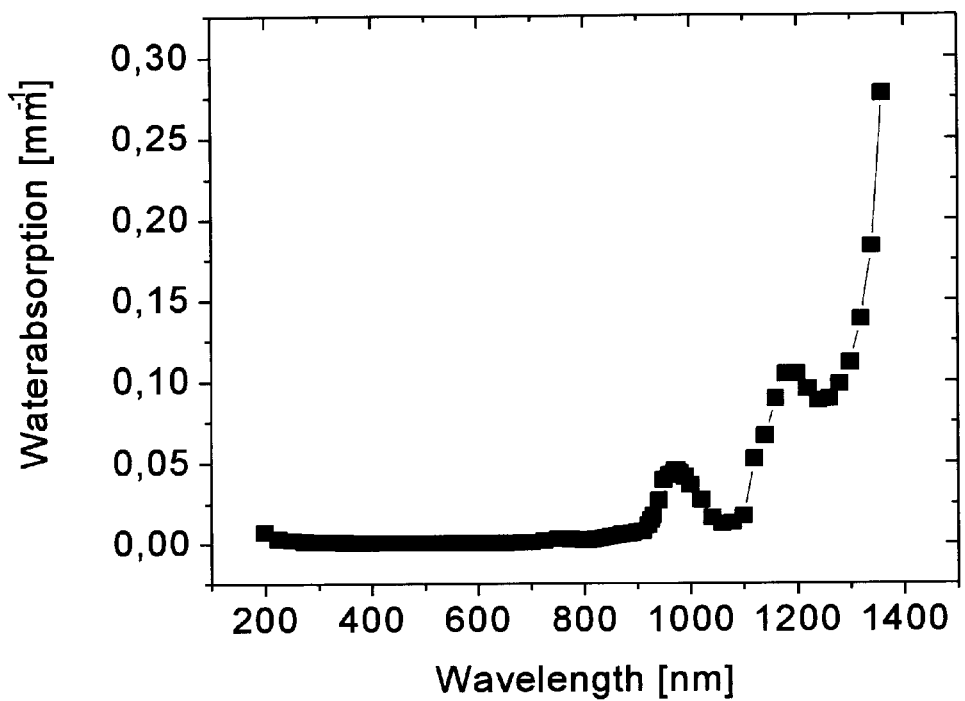
FIG. 1 displays the absorption of water.

The new development of diode lasers, operating in the range of 1000 to 1300 nm region, offers a new laser light source which is suitable to be used for LITT and other medical or cosmetic treatments. These lasers now can be built small in size, and are reliable in practice; and they are now available for a large number of wavelengths in the desired operating range.

Another aspect of this invention is the change of the wavelength during the therapy. Changing the wavelength during the therapy will lead to maximal penetration depth at all times during the operation, although the optical properties change during the operation.

Laser systems for these therapies consist of laser diodes, which are capable of varying their wavelength in the desired range, or alternatively have two or more diode lasers to cover the wavelength range of 1100 nm to 1300 nm, needed for an effective therapy.

Another embodiment of this invention is the possibility to combine more than one applicator (treatment fiber) to be able to treat tumors bigger that 5 cm. One possibility is to distribute the laser power equally on all used applicators. Another option would be to apply different powers to each of the used applicators. Currently the laser power can be delivered from the source over a beam splitter to the treatment fibers. A new possibility, which allows to adjust the power delivered to each treatment fiber, is to use different diode lasers, one for each treatment fiber connected to the laser with a multi-fiber connector. This connector can connect simultaneously two or more treatment fibers to the appropriate laser source. The treatment fibers then combine to one triple-fiber and finally split up again shortly before they reach the treatment area. This new option is useful if large or asymmetric tumors are to be treated.

Another embodiment of the invention would have an individual feedback loop with each applicator to measure the achieved temperature in the tumor. This can be used for regulation and stabilization during the therapy process. The laser source has a control input, which is used to control the laser power output. The signal of the feedback loop reports for example on the actual temperature in the tissue, and can be used to adjust the laser power. This control can be done by a personal computer, which receives the mentioned temperature data and reduces or increases the laser power to have a constant temperature in the tissue during the therapy.

The therapy performed in the wavelength range mentioned above can be applied to all operations where tissue has to be coagulated or to be shrunk. These therapies include cancer treatment, for example brain tumors as mentioned above or liver tumors. Of course benign prostate hyperplasia can also be treated with this technique. One could think of irradiating collagen and cartilage as well. Treatment of corresponding diseases of animals are possible also.

The new features of this invention including the novel attributes and use of combination of parts are now described in detail for a specific example.

In FIG. 1 the absorption of water is shown as a function of the incident wavelength. A first absorption peak is located approximately at 980 nm. Going to higher wavelength there is a local minimum at 1050 nm, where the currently used Nd-YAG laser emits laser light. After this the water absorption is strongly ascending. Since this is not enough to determine the penetration depth in tissue one has to take a look at the following measurements of the optical properties of tissue, too.

Figure 2:
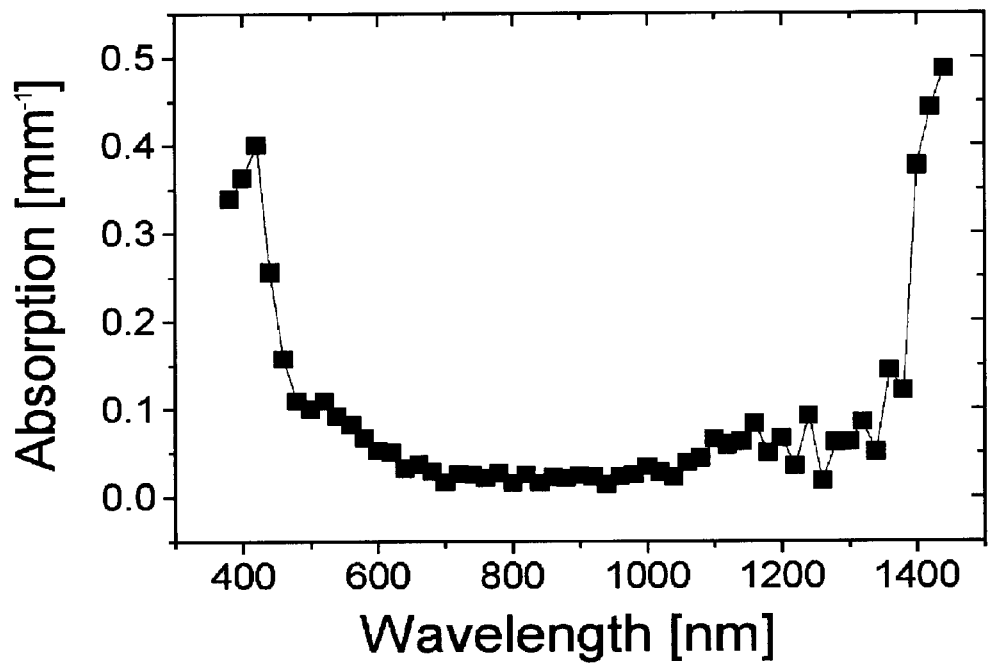
FIG. 2 shows the absorption of a human brain tumor (meningeoma).
Figure 3:
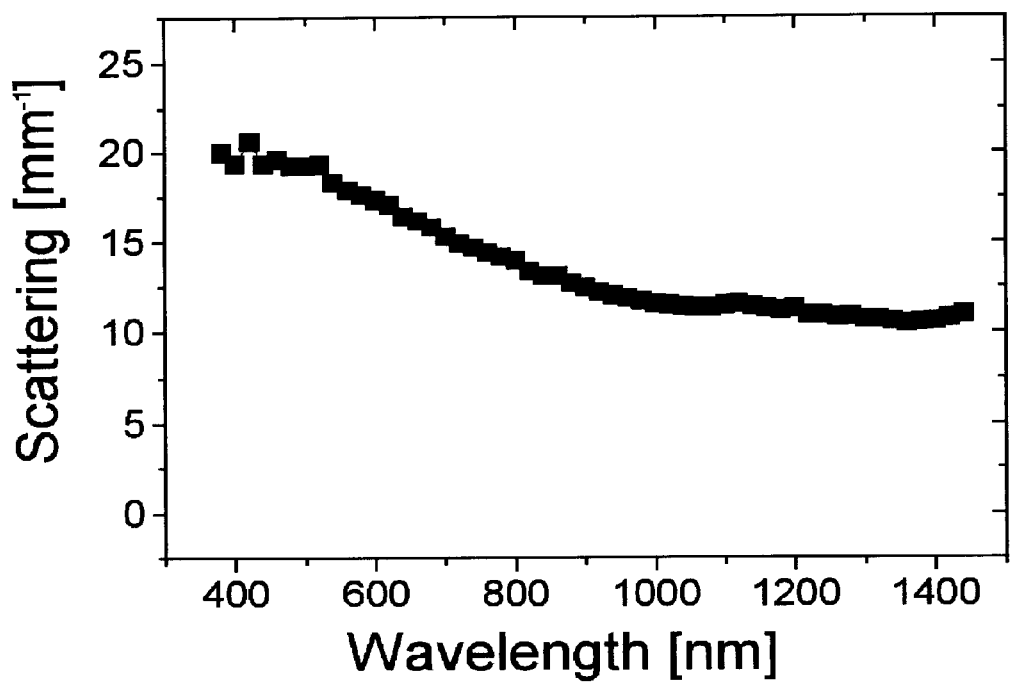
FIG. 3 shows the scattering of a human brain tumor (meningeoma).
Figure 4:
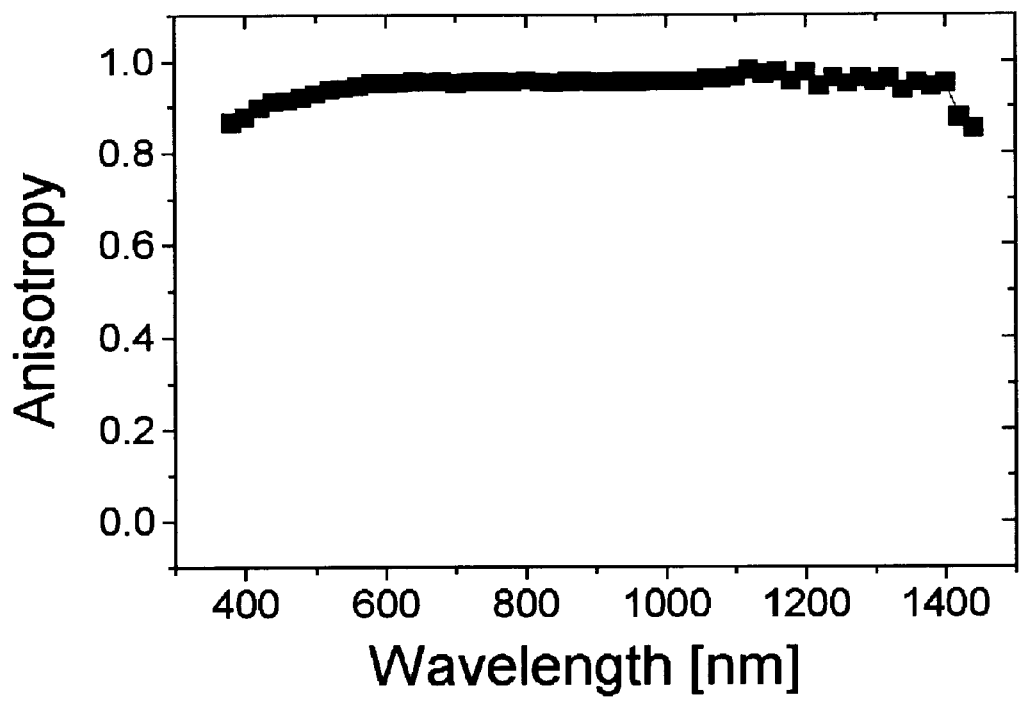
FIG. 4 shows the anisotropy of a human brain tumor (meningeoma).

As one example the absorption coefficient of human brain tumor (meningeoma) is shown as a function of the wavelength in FIG. 2. The absorption of this type of tissue is low in the visible wavelength range. In the near infrared including 1064 nm there is a slight rise in absorption until 1150 nm, after that are some local minimums between 1200 and 1300 nm. Finally the absorption of this type of tumor is rising strongly from 1350 nm. This means that if only absorption would be present the penetration depth would be bigger in the range of 1200 nm to 1300 nm. The range of 800 to 950 nm would not be of use, because absorption in this range is so low, that no significant heating would occur. To have a complete view one has to take scattering into account, too. The scattering shown in FIG. 3 is getting lower with rising wavelength. This means that if only scattering would be present the penetration depth would be bigger for longer wavelengths. The last considered value is the anisotropy factor shown in FIG. 4 which roughly speaking determines the direction of scattering. The values of the anisotropy are roughly uniform in the mentioned wavelength range.

Figure 5:
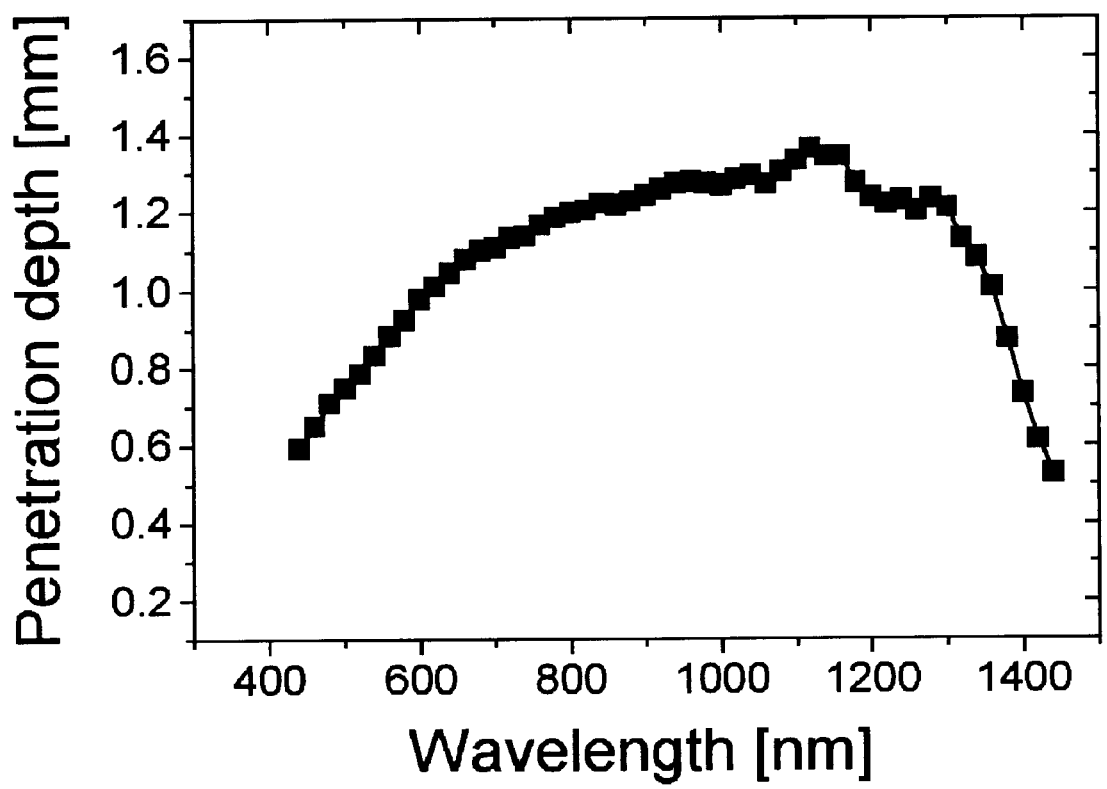
FIG. 5 shows the penetration depth of a human brain tumor (meningeoma).

To obtain the ideal wavelength range one has to combine these three observations. FIG. 5 shows the resulting penetration depth. One can easily see, that the penetration depth is almost uniform in the range of 1000 nm up to 1300 nm, with a maximum between 1100 and 1150 nm. This wavelength range should be used, if maximal penetration depth and maximal lesion sizes need to be induced in tissue.

For many treatments, applications either a single emitter or a group of emitters may function as a unit having one emitting wavelength, activating one process in a tissue or additive such as an absorber or photosensitizer. The group of emitters might be a diode laser bar or a portion of a bar which can be independently powered and thus controlled.

Having described some preferred embodiments of the invention with reference to the accompanying drawings, it is to be understood that the invention is not limited to the precise embodiments, and that various changes and modifications may be effected therein by skilled in the art without departing from the scope or spirit of the invention as defined in the appended claims.

What is claimed is:

1. A medical or cosmetic therapeutic treatment in the thermal regime using a diode laser system comprising at least one laser diode emitter operating at a wavelength between 1000 nm and 1300 nm and emitting sufficient power to thermally destroy tumors and at least one means to optically transmit said emissions to a treatment site, comprising the steps of:

selecting said treatment from a group consisting of coagulating, denaturing and shrinking tissue; and administering said treatment in combination with a chemotherapy treatment.

2. A medical or cosmetic therapeutic treatment according to claim 1, further comprising pretreatment steps of:

administering an absorber; and tuning said laser system to a specific absorption band of said absorber.

3. A medical or cosmetic therapeutic treatment according to claim 1, further comprising a step of:

varying said emission wavelength selectively within a specified range without interrupting said therapeutic treatment.

4. A medical or cosmetic therapeutic treatment according to claim 1, further comprising a step of:

providing active treatment site cooling during said treatment.

5. A medical or cosmetic therapeutic treatment according to claim 1, further comprising a step of:

controlling and stabilizing induced temperature at said treatment site by means of a feedback loop associated with each emitter(emitter group).

6. A medical or cosmetic therapeutic treatment in the thermal regime using a diode laser system comprising at least one laser diode emitter operating at a wavelength between 1000 nm and 1300 nm and emitting sufficient power to thermally destroy tumors and at least one means to optically transmit said emissions to a treatment site, comprising the steps of:

administering an absorber;

tuning said laser system to a specific absorption band of said absorber;

selecting said treatment from a group consisting of coagulating, denaturing and shrinking tissue; and administering said treatment in combination with a radiation therapy treatment.

7. A medical or cosmetic therapeutic treatment according to claim 6, further comprising a step of:

varying said emission wavelength selectively within a specified range without interrupting said therapeutic treatment.

8. A medical or cosmetic therapeutic treatment according to claim 6, further comprising a step of:

providing active treatment site cooling during said treatment.

9. A medical or cosmetic therapeutic treatment according to claim 6, further comprising a step of:

controlling and stabilizing induced temperature at said treatment site by means of a feedback loop associated with each emitter(emitter group).

* * * * *